United States Patent
Mirza et al.

(10) Patent No.: US 9,220,550 B2
(45) Date of Patent: *Dec. 29, 2015

(54) CROSS PIN FIXATOR FOR BONE FRAGMENTS AND USE THEREOF

(71) Applicant: A.M. SURGICAL, INC., Smithtown, NY (US)

(72) Inventors: Romi Mirza, Smithtown, NY (US); Ather Mirza, Smithtown, NY (US)

(73) Assignee: A.M. SURGICAL, INC., Smithtown, NY (US)

( * ) Notice: Subject to any disclaimer, the term of this patent is extended or adjusted under 35 U.S.C. 154(b) by 17 days.

This patent is subject to a terminal disclaimer.

(21) Appl. No.: 14/457,756

(22) Filed: Aug. 12, 2014

(65) Prior Publication Data

US 2014/0350610 A1 Nov. 27, 2014

Related U.S. Application Data

(63) Continuation of application No. 13/350,561, filed on Jan. 13, 2012, now Pat. No. 8,852,248.

(51) Int. Cl.
*A61B 17/80* (2006.01)
*A61B 17/88* (2006.01)

(52) U.S. Cl.
CPC .......... *A61B 17/8061* (2013.01); *A61B 17/8047* (2013.01); *A61B 17/8057* (2013.01); *A61B 17/88* (2013.01)

(58) Field of Classification Search
CPC ........... A61B 17/8047; A61B 17/7059; A61B 17/8042; A61B 17/8057; A61B 17/8605
USPC ........................................... 606/280–299, 59
See application file for complete search history.

(56) References Cited

U.S. PATENT DOCUMENTS

| 5,954,722 | A | 9/1999 | Bono |
| 5,976,141 | A | 11/1999 | Haag et al. |
| 7,524,325 | B2 * | 4/2009 | Khalili .......................... 606/290 |
| 8,668,723 | B2 * | 3/2014 | Altarac .............. A61B 17/7059 606/290 |
| 2001/0037112 | A1 * | 11/2001 | Brace et al. ...................... 606/69 |
| 2002/0013586 | A1 * | 1/2002 | Justis ................. A61B 17/7011 606/255 |

(Continued)

FOREIGN PATENT DOCUMENTS

WO 2005/069752 8/2005

OTHER PUBLICATIONS

International Search Report and Written Opinion of the International Searching authority of International Application No. PCT/US2012/021248, mailed Aug. 22, 2012.

(Continued)

*Primary Examiner* — Mary Hoffman
*Assistant Examiner* — Tara R Carter
(74) *Attorney, Agent, or Firm* — Ping Wang; Andrews Kurth LLP

(57) ABSTRACT

The present application relates to a cross pin fixator device comprising a plate member with spherical cavities that are open to the front and to the back of the plate, collapsible pin holder members having a central channel for insertion of a bone pin, the collapsible pin holder member being press-fit into the spherical cavities, and bone pins individually inserted into the central channel of a pin holder. The application also relates to a method for treating a fracture of the proximal humerus using the proximal humerus cross pin fixator and to a kit for treating a fracture of a bone.

23 Claims, 5 Drawing Sheets

SECTION A-A

(56) References Cited

U.S. PATENT DOCUMENTS

| | | | |
|---|---|---|---|
| 2003/0040749 A1* | 2/2003 | Grabowski | A61B 17/7059 606/71 |
| 2003/0083658 A1* | 5/2003 | Hawkes et al. | 606/61 |
| 2005/0154392 A1* | 7/2005 | Medoff et al. | 606/69 |
| 2008/0300637 A1 | 12/2008 | Austin et al. | |

OTHER PUBLICATIONS

Filed History of U.S. Appl. No. 13/350,561, filed Jan. 13, 2012.

* cited by examiner

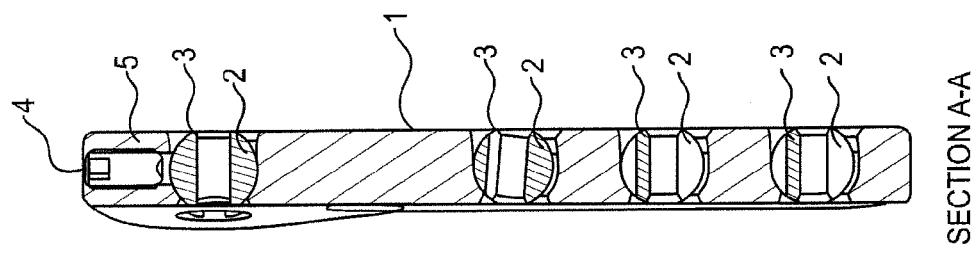
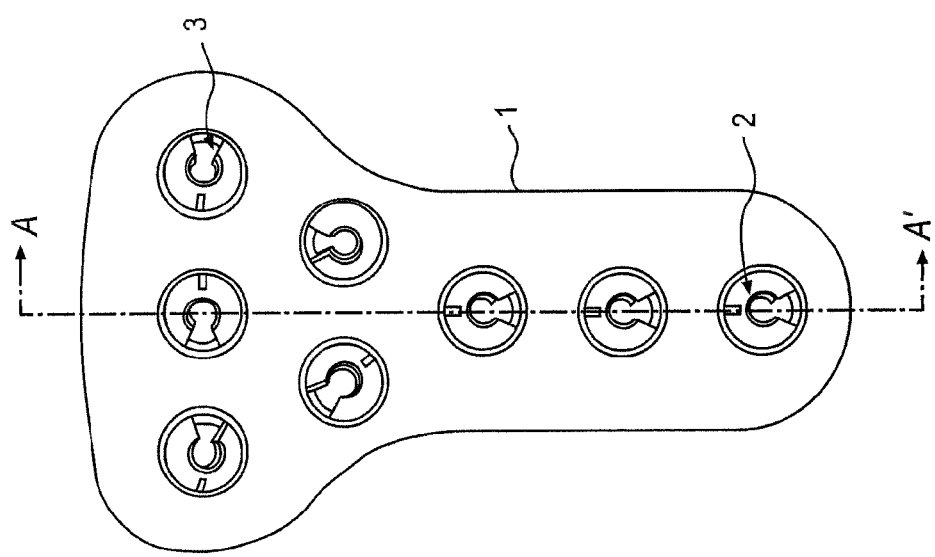

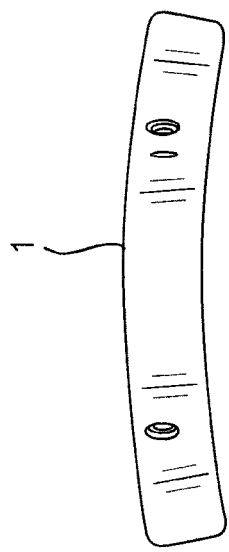
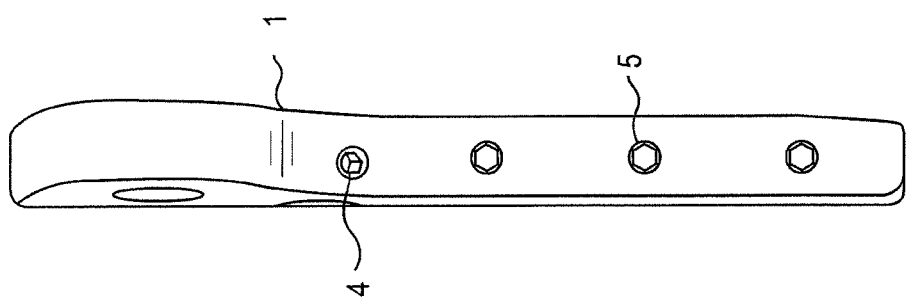
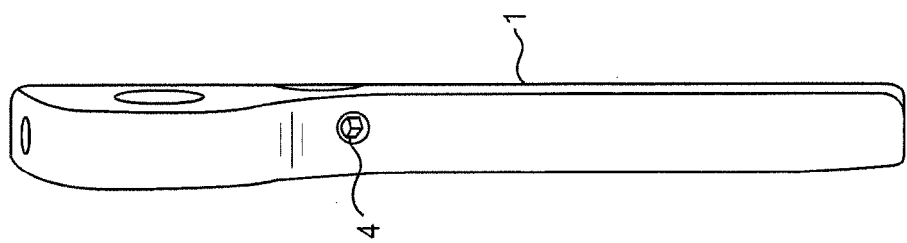

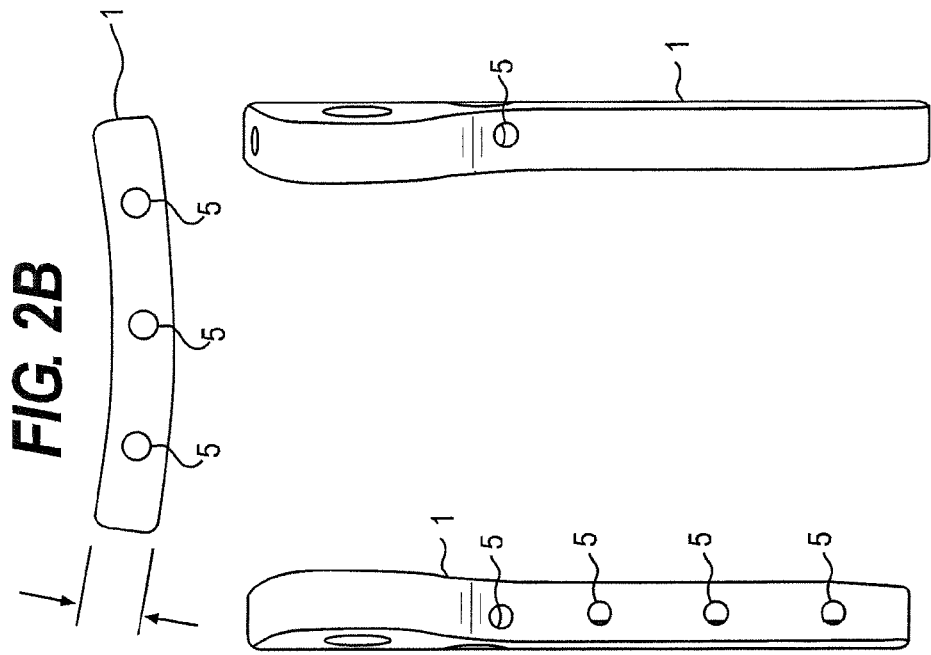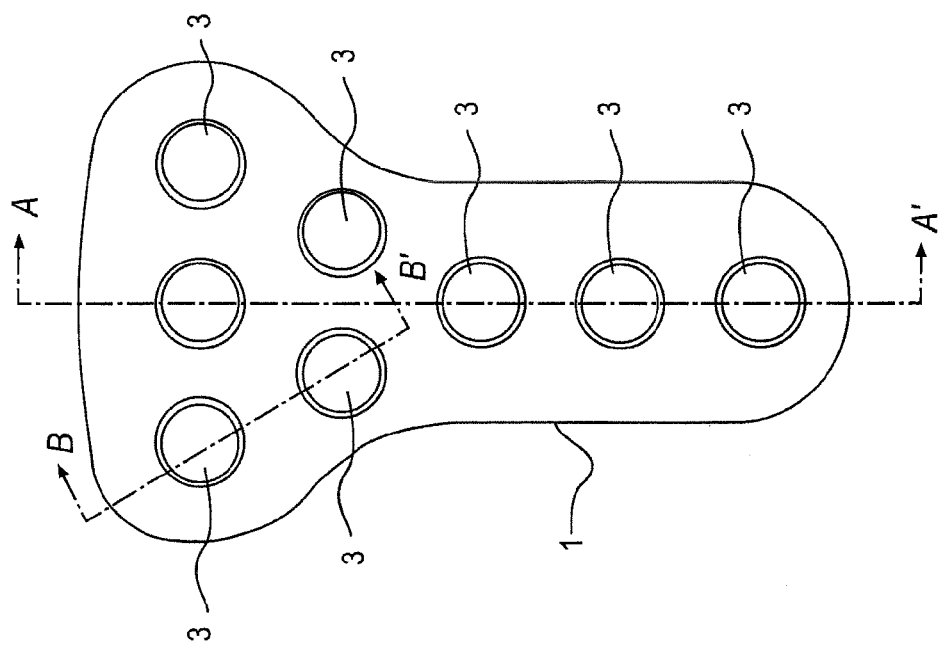

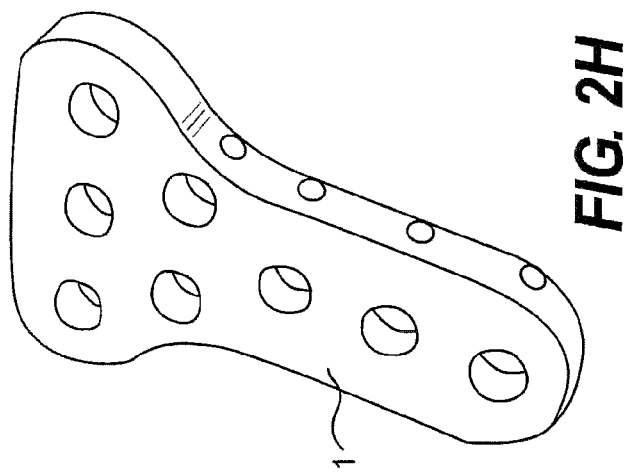
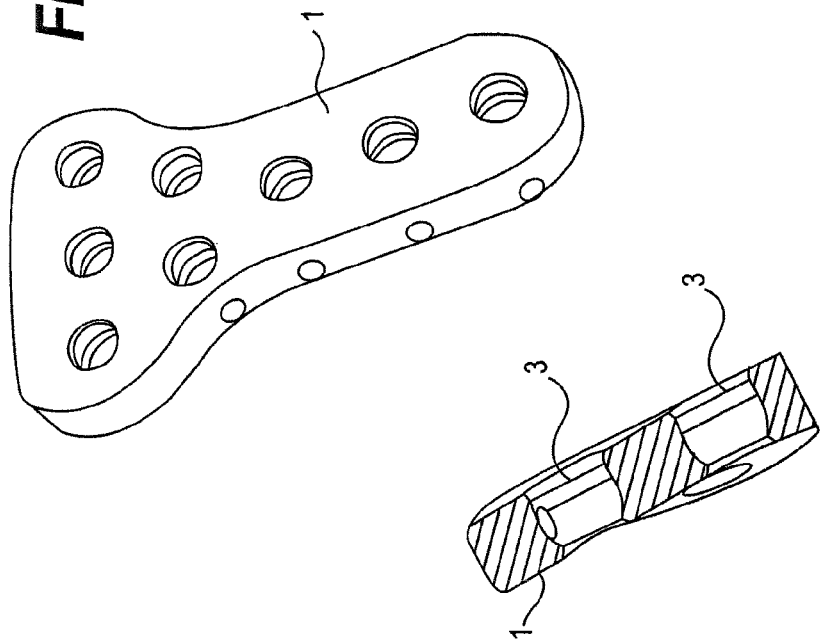
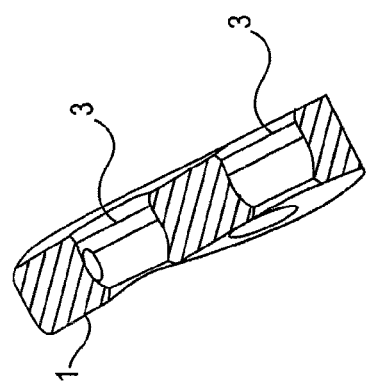
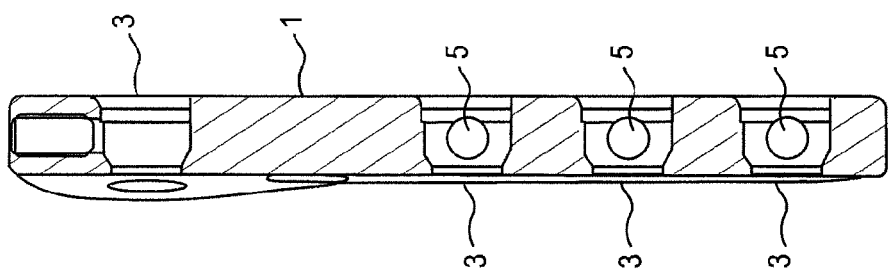

CROSS PIN FIXATOR FOR BONE FRAGMENTS AND USE THEREOF

This application is a Continuation of U.S. application Ser. No. 13/350,561, filed on Jan. 13, 2012. The entirety of the aforementioned applications is incorporated herein by reference.

FIELD

This application generally relates to medical devices. In particular, the application relates to a medical device for immobilizing bone fragments of a fractured bone, such as a fractured proximal humerus.

BACKGROUND

Bone fractures are typically treated by restoring the fractured pieces of bone to their natural positions and maintaining those positions while the bone heals. Briefly, the fractured bone(s) is aligned in good position (also called reduction) and then immobilized with a cast that holds the bones in position and immobilizes the joints above and below the fracture. When the initial post-fracture edema or swelling goes down, the fracture may be placed in a removable brace or orthosis. In cases of complex or open fractures, surgical nails, screws, plates and wires may be used to internally hold the fractured bone together. The surgical implantation of these internal fixation devices, however, may cause extensive trauma to the patient, increase potential for infection, and require second surgery for their removal. An alternative to internal fixation devices is the external fixation device. Pins are placed into the broken bone above and below the fracture site to reposition and immobilize the bone fragments. The pins are connected to a metal bar or bars outside the skin to form a stabilizing frame that holds the bones in the proper position so they can heal. After an appropriate period of time, the external fixation device is removed.

The proximal humerus is part of the shoulder joint, and it also is the attachment of the important rotator cuff muscles. These muscles help with movement of the shoulder, and injury to the proximal humerus can affect the function of these muscles. A proximal humerus fracture is a common injury to the shoulder and are among the most common broken bones. It is not possible to immobilize proximal humerus fractures by placing them in a cast. There still exists a need for lightweight, non-bridging external fixation devices that allows for direct fixation of a proximal humerus fracture, maintenance of the radiological parameters, and early mobilization of the shoulder.

SUMMARY

One aspect of the present application relates to a cross pin fixator device comprising: a plate member having a plurality of spherical cavities that are open to the front and to the back of the plate, a plurality of collapsible pin holder members having a central channel for insertion of a bone pin, wherein each collapsible pin holder member is press-fit into one of the spherical cavities, threaded holes in the plate comprising set screws that immobilize or deform the pin holder members in the cavities, and a plurality of bone pins, wherein each bone pin is inserted into the central channel of a pin holder.

Another aspect of the present application relates to a collapsible, spherical pin holder comprising: a central channel open at the top and the bottom of the pin holder, and a compression gap in the side, of the pin holder, wherein the compression gap is parallel to and connected with the central channel.

Another aspect of the present application relates to a method for treating a fracture of a proximal humerus in a patient comprising: inserting one end of each of a plurality of bone pins through the fracture site, wherein the bone pins traverse the site of the bone fracture in a multi-angle and multi-planar configuration so as to secure fractured bone segments against rotation and axial movement, and inserting the opposite end of each of the plurality of bone pins through a collapsible pin holder member of a proximal humerus cross pin fixator having a central channel for insertion of a bone pin, wherein each collapsible pin holder member is press-fit into a spherical cavity of a plate member of the proximal humerus cross pin fixator.

Another aspect of the present application relates to a kit for the treatment of a fracture of a bone comprising: a plate member of a cross pin fixator device having a plurality of spherical cavities that are open to the front and to the back of the plate, the plate member further having a plurality of threaded holes in the plate for set screws, a plurality of collapsible pin holder members having a central channel for insertion of a bone pin, wherein each collapsible pin holder member can be press-fit into one of the spherical cavities of the plate member, and a plurality of bone pins.

BRIEF DESCRIPTION OF THE DRAWINGS

The accompanying drawings illustrate one or more embodiments of the application and, together with the written description, serve to explain the principles of the application. Wherever possible, the same reference numbers are used throughout the drawings to refer to the same or like elements of an embodiment.

FIGS. 1A-E show different views of an exemplary proximal humerus cross pin fixator.

FIGS. 2A-H show different views of the plate member of the exemplary proximal humerus cross pin fixator.

DETAILED DESCRIPTION

Figure 3E:
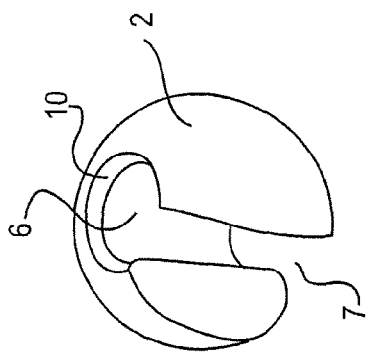
FIGS. 3A-F show views of a pin holder member of the exemplary proximal humerus cross pin fixator.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

The present application relates to an external fixation device for the immobilization of bone fragments of fractured bones. In a preferred embodiment, the external fixation device is a cross pin fixator. In some particular embodiments, the fracture is a simple fracture. In some particular embodiments, the fracture is comminuted. In some particular embodiments, the fracture is displaced. In some particular embodiments, the fracture is non-displaced.

One aspect of the present application relates to a cross pin fixator device comprising: a plate member having a plurality of spherical cavities that are open to the front and to the back of the plate, a plurality of collapsible pin holder members having a central channel for insertion of a bone pin, wherein each collapsible pin holder member is press-fit into one of the spherical cavities, threaded holes in the plate comprising set screws that contact the collapsible pin holder members from the side and immobilize or deform the pin holder members in the cavities, and a plurality of bone pins, wherein each bone pin is inserted into the central channel of a pin holder.

In one particular embodiment, the cross pin fixator device is a proximal humerus cross pin fixator.

In a particular embodiment, the pin holders are retained in the plate by ridges in the plate.

In another particular embodiment, the plate is constituted of a lightweight material. In a related embodiment, the lightweight material is selected from the group consisting of aluminum, aluminum alloy, titanium, titanium alloy and a fiber reinforced polymeric material.

In a further embodiment, the polymeric material is selected from the group consisting of PPS (polyphenylene sulfide), PEEK (polyetherether ketone), Ultrapek (polyether ketone ether ketone), epoxy, polyester, polyamide, and vinyl ester.

In another further embodiment, the fiber is selected from the group consisting of carbon fibers, glass fibers, metal fibers, synthetic fibers, and mixtures thereof.

In another further embodiment, the fiber reinforced polymeric material comprises carbon-fiber reinforced plastic.

In another particular embodiment, the plate is constituted of a high strength material.

In a further embodiment, the high strength material is mineral reinforced plastic. In a related embodiment, the mineral is selected from the group consisting of talc, silica, silicon carbide, zirconia and alumina.

In another further embodiment, the high strength material is a ceramic material. In a related embodiment, the ceramic material is selected from the group consisting of alumina, zirconia, and silicon carbide.

In another further embodiment, the high strength material is steel or steel alloys.

Another aspect of the present application relates to a collapsible, spherical pin holder comprising: a central channel open at the top and the bottom of the pin holder, and a compression gap in the side of the pin holder, wherein the compression gap is parallel to and connected with the central channel.

In a particular embodiment, the spherical pin holder further comprises a slit in the side opposite the compression gap, wherein the slit is parallel to but is not connected with the central channel.

In another embodiment, the spherical pin holder is constituted of polyphenylsulfone.

Another aspect of the present application relates to a method for treating a fracture of a proximal humerus in a patient comprising: inserting one end of each of a plurality of bone pins through the fracture site, wherein the bone pins traverse the site of the bone fracture in a multi-angle and multi-planar configuration so as to secure fractured bone segments against rotation and axial movement, and inserting the opposite end of each of the plurality of bone pins through a collapsible pin holder member of a proximal humerus cross pin fixator having a central channel for insertion of a bone pin, wherein each collapsible pin holder member is press-fit into a spherical cavity of a plate member of the proximal humerus cross pin fixator.

In a particular embodiment, each bone pin is a Kirschner wire.

In another particular embodiment, the method further comprises immobilizing or deforming a collapsible pin holder by tightening a set screw inserted into a threaded hole in the plate member of the proximal humerus cross pin fixator.

Another aspect of the present application relates to a kit for the treatment of a fracture of a bone comprising: a plate member of a cross pin fixator device having a plurality of spherical cavities that are open to the front and to the back of the plate, the plate member further having a plurality of threaded holes in the plate for set screws, a plurality of collapsible pin holder members having a central channel for insertion of a bone pin, wherein each collapsible pin holder member can be press-fit into one of the spherical cavities of the plate member, and a plurality of bone pins.

The cross pin fixator device of the present application can be adapted to a shape and size to immobilize fragments of any fractured bone in a mammalian body. In a particular embodiment, said mammal is a human.

In particular embodiments, the bone is a long bone, having a shaft and two extremities. Long bones are found in the limbs and include the clavicle, humerus, radius, ulna, femur, tibia, fibula, metacarpal and metatarsal bones.

As used herein, the "proximal" end of a long bone refers to the extremity of the bone closest to the center of the body when the limb is extended. As used herein, the "distal" end of a long bone refers to the extremity of the bone farthest from the center of the body when the limb is extended. The cross pin fixator device of the present application may be specifically configured to immobilize the fragments of a fracture at the proximal end of a long bone, the distal end of a long bone, or the shaft of a long bone, or a combination thereof. In some embodiments, the cross pin fixator device may span across a joint between two long bones, immobilizing the fragments of the fractured distal end of one long bone and the fragments of the fractured proximal end of an adjacent long bone.

In other particular embodiments, the cross pin fixator device of the present application can be configured to immobilize the fragments of a fractured short bone, including the patella, sesamoid, carpal and tarsal bones.

In further particular embodiments, the cross pin fixator device of the present application can be configured to immobilize the fragments of a fractured flat bone, including the skull, cranium, occipital, parietal, frontal, nasal, lachrymal, vomer, scapula, os innominatum, sternum, and rib bones.

In additional particular embodiments, the cross pin fixator device of the present application can be configured to immobilize the fragments of a fractured irregular bone, including the vertebrae, sacrum, coccyx, temporal, sphenoid, ethmoid, malar, superior maxillary, inferior maxillary, palate, inferior turbinated, and hyoid bones. In particular embodiments, the cross pin fixator device spans across multiple vertebrae, including any portion of the vertebral column, the cervical vertebrae, and/or the dorsal vertebrae, and/or the lumbar vertebrae, and/or the sacral vertebrae, and/or the coccygeal vertebrae or the entire vertebral column.

In some embodiments, the cross pin fixator device of the present application may span across between any two or more adjacent bones, immobilizing the fragments of the fractured bones. In particular embodiments, the cross pin fixator device of the present application may span across between any two, three, four, five, six, seven, eight, nine, 10, 11, 12, 13, 14, 15, 16, 16, 18, 19, 20, 21, 22, 23, 24, 25, 26, 27, 28, 29, 30, 31, 32 or 33 adjacent bones, immobilizing the fragments. In some embodiments, the bones are adjacent linearly, such as the vertebrae. In some embodiments, the bones are adjacent side by side, such as the metacarpals or metatarsals.

In some embodiments, one region of the cross pin fixator device of the present application is attached to at least one non-fractured bone in order to provide stability to immobilized fragments of a fractured adjacent bone attached to another region of the cross pin fixator device.

For purposes of describing the cross pin fixator device of the present application, a proximal humerus cross pin fixator is exemplified and the following terms are used:

As used herein, the "top" refers to the end of the device that is oriented towards the ball or head of the humerus.

As used herein, the "bottom" refers to the end of the device that is oriented towards the shaft of the humerus.

As used herein, the "inside" or "back" refers to the face of the device that is oriented towards the body of the patient.

As used herein, the "outside" or "front" refers to the face of the device that is oriented away from the body of the patient.

As used herein, the "side" refers to surfaces around the perimeter of the device joining the outside face to the inside face.

In some embodiments, the proximal humerus cross pin fixator device is indicated for simple and comminuted, displaced and/or non-displaced fractures of the proximal humerus.

FIG. 1A shows a face of the plate 1 comprising a plurality of collapsible pin holders 2 that are individually press-fit into individual cavities 3 in the plate 1. The cavities 3 are open to the inside and outside faces of the plate 1 and each pin holder 2 can freely rotate inside the cavity 3.

FIG. 1B shows a cross section of the device along the line A-A' in FIG. 1A. Pin holders 2 can be seen located in cavities 3 in the plate 1. Each pin holder 2 can be seen to be spherical in shape and comprises a central channel for the insertion of a bone pin or screw. Each bone pin is driven into a bone fragment and threaded though an individual pin holder 2 of the device. Each cavity 3 is also spherical in shape to allow the pin holder 2 to freely rotate within the cavity 3. Additionally, each cavity 3 comprises ridges at the inside and outside faces of the plate 1 to hold the collapsible spherical pin holder 2 in the cavity 3 after it is press-fit into said cavity 3.

Additionally in FIG. 1B, a set screw 4 is shown in a threaded hole 5 that contacts a cavity 3. Each threaded hole 5 is located open at one end to the side of the device and at the other end to a cavity 3. The set screw 4 is screwed into the threaded hole 5 in order to contact the collapsible pin holder 2 from the side. The contact of the set screw 4 with the pin holder 2 immobilizes the pin holder in the cavity 3 from the side and deforms the pin holder 2 such that a pin that is secured into a bone fragment is held in place by the device. In a particular embodiment, each cavity 3 is contiguous with at least one threaded hole 5 and at least one set screw 4 is used to immobilize or deform each collapsible pin holder 2 from the side.

FIGS. 1C and 1D depict side aspect views between the top and bottom of the device showing the plate 1 along with set screws 4 and threaded holes 5. In a particular embodiment, the set screw 4 is completely recessed within the threaded hole 5. In another embodiment, the head of the set screw 4 protrudes from the threaded hole 5. In a particular embodiment, the head of the set screw 4 is adapted to be driven with a screwdriver or bit selected from the group consisting of flat-bladed, triangular, square, Philips, hex, TORX, or star-shaped.

FIG. 1E is an end view of the device from the bottom side showing the plate 1. In a particular embodiment, the plate 1 is curved such that the inside face is concave and the outside face is convex. In another embodiment, the plate 1 is flat. In another embodiment, the edges of the plate 1 or at least a portion thereof is angled towards the inside of the device.

In addition, the proximal humerus cross pin fixator of the present application uses small diameter bone pins that flex and allow lead sharing across the fracture fragments, facilitating callus formation and reducing the risk of nonunion. Also, the cross positioning of bone pins fixes the larger fracture fragments while buttressing the smaller fragments, helping to maintain joint congruency.

In a particular embodiment, the bone pin is constituted of a surgical grade metal. In another particular embodiment, the bone pin is a Kirschner wire (K-wire). In a further embodiment, the K-wire is between about 1 mm and about 6 mm in diameter. In a still further embodiment, the K-wire is between about 3 mm and about 5 mm in diameter. In a yet further embodiment, the K-wire is about 4 mm in diameter.

FIGS. 2A-H show aspect views of the plate 1 of the external proximal humerus cross pin fixator. FIG. 2A shows a face of the plate 1 member, having a plurality of cavities 3 for the placement of pin holders. In a particular embodiment, the plate is made of a lightweight material. In a further embodiment, the lightweight material is aluminum or an aluminum alloy. In another further embodiment, the lightweight material is titanium or a titanium alloy.

In another further embodiment, the lightweight material is a fiber reinforced lightweight polymeric material.

In one embodiment, the polymeric material is selected from the group consisting of PPS (polyphenylene sulfide), PEEK (polyetherether ketone), Ultrapek (polyether ketone ether ketone), epoxy, polyester, polyamide, and vinyl ester.

In another embodiment, the fiber is selected from the group consisting of carbon fibers, glass fibers, metal fibers, synthetic fibers, and mixtures thereof.

In another embodiment, the fiber reinforced polymeric material is a carbon-fiber reinforced plastic.

In a related embodiment, the carbon-fiber reinforced plastic has a minimal tensile strength equal to or greater than 30 Ksi.

In another related embodiment, the carbon-fiber reinforced plastic is PPS reinforced with 40-60% of carbon fiber.

In another related embodiment, the carbon-fiber reinforced plastic is PEEK reinforced with 30-50% of carbon fiber.

In another related embodiment, the carbon-fiber reinforced plastic is epoxy reinforced with 30-60% of carbon fiber.

In another particular embodiment, the plate is made from a high strength material.

In a further embodiment, the high strength material is mineral reinforced plastic. In a related embodiment, the mineral is selected from the group consisting of talc, silica, silicon carbide, zirconia and alumina.

In another further embodiment, the high strength material is a ceramic material. In a related embodiment, the ceramic material is selected from the group consisting of alumina, zirconia, and silicon carbide.

In another further embodiment, the said high strength material is steel or steel alloys.

FIG. 2B shows an end-view of the top side of the plate 1 having threaded holes 5 for the insertion of set screws.

FIGS. 2C and 2D show side views between the top and bottom of the plate 1 having threaded holes 5 for the insertion of set screws.

FIG. 2E shows a cross section of the device along the line A-A' in FIG. 2A. The spherically shaped cavities 3 can be seen in the plate 1. Each cavity 3 comprises ridges at the inside and outside faces of the plate 1 to hold the collapsible spherical pin holder in the cavity 3 after it is press-fit into said cavity 3. The threaded holes 5 for the insertion of set screws are shown to be contiguous with the cavities 3 so that the set screws can contact the spherical pin holders for immobilization or deforming.

FIG. 2F shows a cross section of the device along the line B-B' in FIG. 2A. The spherically shaped cavities 3 can be seen in the plate 1. Each cavity 3 comprises ridges at the inside and outside faces of the plate 1 to hold the collapsible spherical pin holder in the cavity 3 after it is press-fit into said cavity 3.

FIGS. 2G and 2H are perspective views of the plate 1 showing the inside and outside faces, respectively.

Figure 3F:
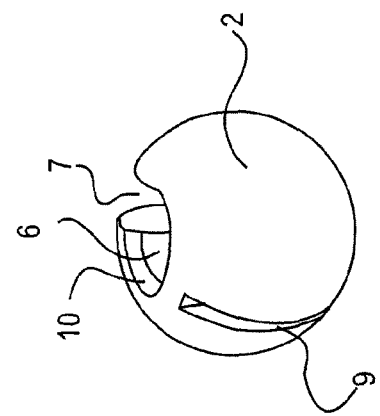
Figure 3C:
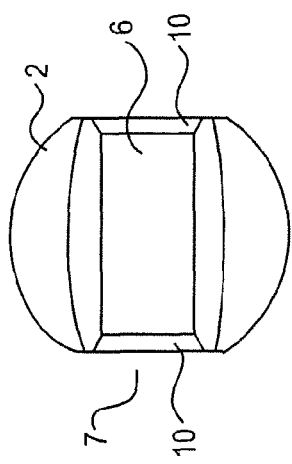
Figure 3D:
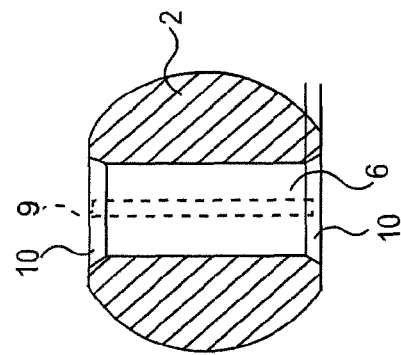
Figure 3A:
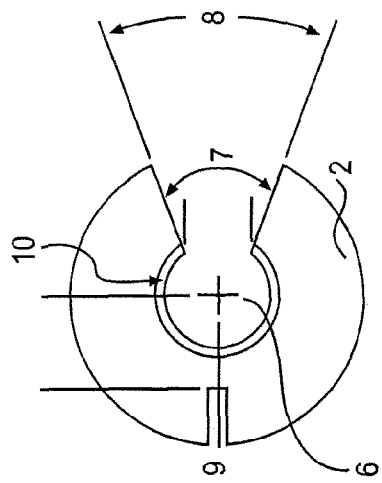

FIGS. 3A-F are views of the collapsible spherical pin holder 2 member of the device. FIG. 3A is a view from the top of a collapsible spherical pin holder 2 member of the device. The pin holder comprises a central channel 6 for the insertion of a bone pin or screw. The bone pin is embedded in a fragment of the fractured bone and is threaded through the central channel 6 of the pin holder 2 in order to secure the bone pin to the proximal humerus cross pin fixator. In a particular embodiment, the pin holder 2 comprises a compression gap 7 in the side of the sphere that is contiguous with the central channel 6 in order to allow compression of the sphere. In a related embodiment, the compression gap 7 is wedge-shaped. In a further embodiment, the angle of the wedge is between about 20 degrees and about 60 degrees. In a still further embodiment, the angle of the wedge is between about 30 degrees and about 50 degrees. In a still further embodiment, the angle of the wedge is between about 35 degrees and about 45 degrees. In a still further embodiment, the angle of the wedge is about 40 degrees.

Still referring to FIG. 3A, in some embodiments, the pin holder 2 further comprises a slit 9 in the side of the pin holder 2 opposite of the compression gap 7. The slit 9 does not penetrate through the body of the pin holder 2.

In a particular embodiment, the top and bottom ends of the central channel 6 are beveled 10 to ease the threading of the bone pin into the pin holder 2.

In a particular embodiment, the pin holders are made of polyphenylsulfone. [Dr. Mirza: are there any other materials that should be listed here for the pin holders?]

Figure 3B:
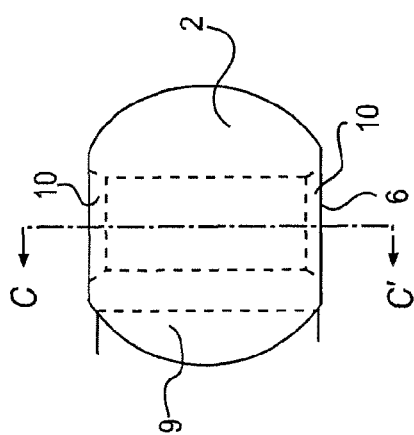

FIG. 3B shows a side view of a pin holder 2 of the device. The dashed lines indicated the relative positions of the central channel 6, slit 9, and beveling 10 within the body of the pin holder 2.

FIG. 3C shows a frontal view of a pin holder 2 of the device. The drawing shows the central channel 6 and the bevels 10 at the top and bottom of the central channel 6 as viewed through the compression gap 7.

FIG. 3D shows a cross section of a pin holder 2 along the line C-C' in FIG. 3B. The drawing shows the central channel 6 and the bevels 10 at the top and bottom of the central channel 6. The dashed lines indicated the relative position of the slit 9 within the body of the pin holder 2 behind the central channel 6.

FIGS. 3E and 3F are perspective views generally showing the front and back, respectively, of a pin holder 2.

Another aspect of the present application relates to a method for the treatment of a fracture of the proximal humerus. The method comprises embedding bone pins into fragments of the fractured proximal humerus and threading the bone pins through collapsible pin holders in a proximal humerus cross pin fixator as described herein. The rotational position of each collapsible pin holder is secured in the device and the bone pin is immobilized in the collapsible pin holder by tightening a set screw against the side of the collapsible pin holder.

In some embodiments, the length of a bone pin protruding from the outside face of the device is trimmed or cut flush with the outside face after the bone pin is immobilized in the collapsible pin holder.

Another aspect of the present application relates to a kit for the treatment of a fracture of the proximal humerus comprising: a plate member of a proximal humerus cross pin fixator having a plurality of spherical cavities that are open to the front and to the back of the plate, the plate member further having a plurality of threaded holes in the plate for set screws, a plurality of collapsible pin holder members having a central channel for insertion of a bone pin, wherein each collapsible pin holder member can be press-fit into one of the spherical cavities of the plate member, and a plurality of bone pins.

In a particular embodiment, the kit further includes a tissue protector. In another particular embodiment, the kit comprises a tool for tightening the set screws.

The contents of all references, patents and published patent applications cited throughout this application, as well as the Figures and Tables, are incorporated herein by reference.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A cross pin fixator device comprising:
    a plate member having front and back faces comprising a plurality of spherical cavities, each cavity being open from the front face to the back face of the plate member;
    a plurality of collapsible pin holder members having a central channel for insertion of a bone pin, wherein each collapsible pin holder member is press-fit into one of the spherical cavities; and
    threaded holes perpendicularly extending from a side of the plate member into the spherical cavities, the threaded holes comprising set screws that contact the collapsible pin holder members from the side of the plate member and immobilize or deform the pin holder members in the cavities.

2. The cross pin fixator device of claim 1, wherein the device is a proximal humerus cross pin fixator.

3. The cross pin fixator device of claim 1, wherein the pin holders are retained in the plate by ridges in the plate.

4. The cross pin fixator device of claim 1, wherein the each pin holder is configured to freely rotate inside a cavity.

5. The cross pin fixator device of claim 1, wherein the plate is constituted of a lightweight material is selected from the group consisting of aluminum, aluminum alloy, titanium, titanium alloy and a fiber reinforced polymeric material.

6. The cross pin fixator device of claim 5, wherein the polymeric material is selected from the group consisting of PPS (polyphenylene sulfide), PEEK (polyetherether ketone), Ultrapek (polyether ketone ether ketone), epoxy, polyester, polyamide, and vinyl ester.

7. The cross pin fixator device of claim 5, wherein the fiber is selected from the group consisting of carbon fibers, glass fibers, metal fibers, synthetic fibers, and mixtures thereof.

8. The cross pin fixator device of claim 5, wherein the fiber reinforced polymeric material comprises carbon-fiber reinforced plastic.

9. The cross pin fixator device of claim 1, wherein the plate is constituted of a high strength material.

10. The cross pin fixator device of claim 9, wherein the high strength material is mineral reinforced plastic.

11. The cross pin fixator device of claim 10, wherein the mineral is selected from the group consisting of talc, silica, silicon carbide, zirconia and alumina.

12. The cross pin fixator device of claim 9, wherein the high strength material is a ceramic material.

13. The cross pin fixator device of claim 12, wherein the ceramic material is selected from the group consisting of alumina, zirconia, and silicon carbide.

14. The cross pin fixator device of claim 9, wherein the high strength material is steel or steel alloys.

15. A method for treating a fracture of a proximal humerus in a patient comprising:

inserting one end of each of a plurality of bone pins through a site of bone fracture, wherein the bone pins traverse the site of bone fracture in a multi-angle and multi-planar configuration so as to secure fractured bone segments against rotation and axial movement;

inserting the opposite end of each of the plurality of bone pins through a collapsible pin holder member of a proximal humerus cross pin fixator having a central channel for insertion of a bone pin, wherein each collapsible pin holder member is press-fit into a spherical cavity of a plate member of the proximal humerus cross pin fixator; and immobilizing a collapsible pin holder by tightening a set screw inserted into a threaded hole in the plate member of the proximal humerus cross pin fixator;

wherein the set screw contacts the collapsible pin holder from the side and immobilizes or deforms the pin holder member in the cavity.

16. The method of claim 15, wherein each bone pin is a Kirschner wire.

17. The method of claim 15, wherein each pin holder is retained in the plate by ridges in the plate and is configured to freely rotate inside the cavity.

18. The method of claim 15, wherein the plate is constituted of a lightweight material selected from the group consisting of aluminum, aluminum alloy, titanium, titanium alloy and a fiber reinforced polymeric material, wherein the polymeric material is selected from the group consisting of PPS (polyphenylene sulfide), PEEK (polyetherether ketone), Ultrapek (polyether ketone ether ketone), epoxy, polyester, polyamide, and vinyl ester.

19. The method of claim 18, wherein the fiber is selected from the group consisting of carbon fibers, glass fibers, metal fibers, synthetic fibers, and mixtures thereof.

20. The method of claim 15, wherein the plate comprises a high strength material comprising mineral reinforced plastic, ceramic material, steel or a steel alloy, wherein the mineral is selected from the group consisting of talc, silica, silicon carbide, zirconia and alumina and wherein the ceramic material is selected from the group consisting of alumina, zirconia, and silicon carbide.

21. A kit for the treatment of a fracture of a bone, comprising:

a plate member of a cross pin fixator having front and back faces comprising a plurality of spherical cavities, each cavity being open from the front face to the back face of the plate member, the plate member further having a plurality of threaded holes perpendicularly extending from a side of the plate into the spherical cavities, the threaded holes configured for fastening a plurality of set screws that, when fastened, contact collapsible pin holder members from the side of the plate member and immobilize or deform the pin holder members in the cavities;

a plurality of collapsible pin holder members having a central channel for insertion of a bone pin, wherein each collapsible pin holder member can be press-fit into one of the spherical cavities of the plate member; and a plurality of bone pins.

22. The cross pin fixator device of claim 1, further comprising a plurality of bone pins, wherein each bone pin is inserted into the central channel of a pin holder.

23. The cross pin fixator device of claim 22, wherein the plurality of bone pins are Kirschner wires.

\* \* \* \* \*